(12) United States Patent
Matsushima et al.

(10) Patent No.: US 9,883,669 B2
(45) Date of Patent: Feb. 6, 2018

(54) MAINTENANCE MEDIUM FOR PRIMATE PLURIPOTENT STEM CELLS

(71) Applicant: BOURBON CORPORATION, Kashiwazaki-shi, Niigata-ken (JP)

(72) Inventors: Akito Matsushima, Matsumoto (JP); Sakiko Takizawa, Matsumoto (JP); Tadayuki Yokoyama, Matsumoto (JP)

(73) Assignee: BOURBON CORPORATION, Kashiwazaki-shi (JP)

( * ) Notice: Subject to any disclaimer, the term of this patent is extended or adjusted under 35 U.S.C. 154(b) by 52 days.

(21) Appl. No.: 14/939,442

(22) Filed: Nov. 12, 2015

(65) Prior Publication Data
US 2016/0143267 A1    May 26, 2016

Related U.S. Application Data

(62) Division of application No. 14/283,649, filed on May 21, 2014, now abandoned.

(51) Int. Cl.
| | | |
|---|---|---|
| *C12N 5/00* | (2006.01) | |
| *A01N 1/02* | (2006.01) | |
| *C12N 5/074* | (2010.01) | |

(52) U.S. Cl.
CPC .......... *A01N 1/0226* (2013.01); *A01N 1/0221* (2013.01); *C12N 5/0696* (2013.01); *C12N 2500/34* (2013.01); *C12N 2501/00* (2013.01)

(58) Field of Classification Search
USPC ........................................................ 435/325
See application file for complete search history.

(56) References Cited

FOREIGN PATENT DOCUMENTS

| | | |
|---|---|---|
| JP | 2013-236558 A | 11/2013 |
| WO | 2011/058558 A2 | 5/2011 |

OTHER PUBLICATIONS

Takizawa-Shirasawa (The 6th International Niigata Symposium on Diet and Health. 2012, p. 152).*
Takahashi (Plos One, 2009, vol. 4, No. 12, e 8067, p. 1-6).*
Yokoyama (The 8th Congress of the Japanese Society for Regenerative Medicine. 2009, vol. 8, p. 221).*
Takizawa-Shirasawa ("New Function and Application of Xylose as a cell culture solution", International Soc. For Stem Cell Res. Poster Abstracts, 11th Annual Meeting Jun. 12-15, 2013, Boston, Mass, USA).*
Jul. 25, 2016 Office Action issued in U.S. Appl. No. 14/283,649.
Jan. 22, 2016 Office Action issued in U.S. Appl. No. 14/283,649.
Yokoyama et al., "Effects of Various Sugars on Cell Proliferation and EB Formation of Mouse ES Cells," The 7th Congress of the Japanese Society for Regenerative Medicine, 2008, vol. 7, pp. 239 (with translation).
Yokoyama et al., "Xylose Maintains the Undifferentiation Status of Mouse ES Cells," The 8th Congress of the Japanese Society for Regenerative Medicine, 2009, vol. 8, pp. 221 (with translation).
Takizawa-Shirasawa et al., "Novel Functions of Xylose to Maintain Slow Proliferation and Undifferentiated State of ES Cells," The 6th International Niigata Symposium on Diet and Health, 2012, pp. 152.
Takizawa-Shirasawa et al., "New Function and Application of Xylose As a Cell Culture Solution," International Society for Stem Cell Research Poster Abstracts, 11th Annual Meeting Jun. 12-15, 2013, Boston, Massachusetts, USA.
Jul. 7, 2015 Information Offer Form issued in JP 2012-109981.
David Runquist et al., "Increased expression of the oxidative pentose phosphate pathway and gluconeogenesis in anerobically growing xylose-utilizing *Saccharomyces cerevisiae*, " Microbial Cell Factories, 2009, 8:49.
Experimental Medicine (separate volume), Cell Culture Protocol Selectable Depending on Purpose, Yodosha, Co., Ltd., p. 212, Mar. 20, 2012.
Mar. 11, 2016 Notification of Reason for Rejection issued in Japanese Application No. 2012-109981.

* cited by examiner

*Primary Examiner* — Michael C Wilson
(74) *Attorney, Agent, or Firm* — Oliff PLC

(57) ABSTRACT

Provided are a maintenance medium for primate pluripotent stem cells, and a method for preserving and a method for controlling proliferation of primate pluripotent stem cells using the medium. The maintenance medium for human pluripotent stem cells according to the present invention includes xylose as a saccharide.

13 Claims, 16 Drawing Sheets
(2 of 16 Drawing Sheet(s) Filed in Color)

SEQUENCE LISTING

```
<160> NUMBER OF SEQ ID NOS: 14

<210> SEQ ID NO 1
<211> LENGTH: 22
<212> TYPE: DNA
<213> ORGANISM: Artificial Sequence
<220> FEATURE:
<223> OTHER INFORMATION: Synthetic Construct - Primer

<400> SEQUENCE: 1
tctatttggg aaggtattca gc                                             22

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct - Primer

<400> SEQUENCE: 2
attgttgtca gcttcctcca                                                20

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct - Primer

<400> SEQUENCE: 3
agctacaaac aggtgaagac                                                20

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct - Primer

<400> SEQUENCE: 4
ggtggtagga agagtaaagg                                                20

<210> SEQ ID NO 5
<211> LENGTH: 19
<212> TYPE: DNA
<213> ORGANISM: Artificial Sequence
<220> FEATURE:
<223> OTHER INFORMATION: Synthetic Construct - Primer
```

```
<400> SEQUENCE: 5
agacatcatc cgcgaccta                                                19

<210> SEQ ID NO 6
<211> LENGTH: 21
<212> TYPE: DNA
<213> ORGANISM: Artificial Sequence
<220> FEATURE:
<223> OTHER INFORMATION: Synthetic Construct - Primer

<400> SEQUENCE: 6
caaaagcaaa cgtccagttc t                                             21

<210> SEQ ID NO 7
<211> LENGTH: 21
<212> TYPE: DNA
<213> ORGANISM: Artificial Sequence
<220> FEATURE:
<223> OTHER INFORMATION: Synthetic Construct - Primer

<400> SEQUENCE: 7
gggggaatgg accttgtata g                                             21

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct - Primer

<400> SEQUENCE: 8
gcaaagctcc taccgtacca                                               20

<210> SEQ ID NO 9
<211> LENGTH: 19
<212> TYPE: DNA
<213> ORGANISM: Artificial Sequence
<220> FEATURE:
<223> OTHER INFORMATION: Synthetic Construct - Primer

<400> SEQUENCE: 9
gaacgggctc gtccactac                                                19

<210> SEQ ID NO 10
<211> LENGTH: 18
<212> TYPE: DNA
<213> ORGANISM: Artificial Sequence
<220> FEATURE:
<223> OTHER INFORMATION: Synthetic Construct - Primer

<400> SEQUENCE: 10
ccccaggaac caaggagt                                                 18

<210> SEQ ID NO 11
<211> LENGTH: 19
<212> TYPE: DNA
<213> ORGANISM: Artificial Sequence
<220> FEATURE:
<223> OTHER INFORMATION: Synthetic Construct - Primer

<400> SEQUENCE: 11
cccaagccca tctactcgt                                                19

<210> SEQ ID NO 12
<211> LENGTH: 21
```

```
<212> TYPE: DNA
<213> ORGANISM: Artificial Sequence
<220> FEATURE:
<223> OTHER INFORMATION: Synthetic Construct - Primer

<400> SEQUENCE: 12
gtaggggaag tgctccttca t                                              21

<210> SEQ ID NO 13
<211> LENGTH: 25
<212> TYPE: DNA
<213> ORGANISM: Artificial Sequence
<220> FEATURE:
<223> OTHER INFORMATION: Synthetic Construct - Primer

<400> SEQUENCE: 13
catccgtaaa gacctctatg ccaac                                          25

<210> SEQ ID NO 14
<211> LENGTH: 19
<212> TYPE: DNA
<213> ORGANISM: Artificial Sequence
<220> FEATURE:
<223> OTHER INFORMATION: Synthetic Construct - Primer

<400> SEQUENCE: 14
atggagccac cgatccaca                                                 19
```

MAINTENANCE MEDIUM FOR PRIMATE PLURIPOTENT STEM CELLS

This is a Divisional of application Ser. No. 14/283,649 filed May 21, 2014. The entire disclosures of the prior applications are hereby incorporated by reference herein in their entirety.

BACKGROUND OF THE INVENTION

Field of the Invention

The present invention relates to a maintenance medium for primate pluripotent stem cells, comprising xylose.

Description of the Related Art

Pluripotent stem cells such as human ES cells (embryonic stem cells) and iPS cells (induced pluripotent stem cells) have been expected to be used and applied in various fields including regenerative medicine and cell therapy because they have the ability to be differentiated into various cells or tissues such as nerve cells and cardiac muscle cells, i.e., pluripotency. Pluripotent stem cells can be grown by culture after cell establishment. However, in pluripotent stem cells of primates including humans, it is not easy to grow the cells while maintaining the cell-specific properties, i.e., undifferentiation status and pluripotency (multipotency).

In order to grow human ES cells or human iPS cells while maintaining the undifferentiation status and the pluripotency, it is usually needed to culture these cells in coexistence with feeder cells, or to add substances for maintaining undifferentiation status, for example, ascorbic acid, basic fibroblast growth factor (bFGF), and transforming growth factor β-3 (TGF-β3), to a medium (refer to WO 2011/058558). However, the passage process in culture in coexistence with feeder cells is complicated, and many of substances for maintaining undifferentiation status are expensive. In addition, for human iPS cells, since it is known that the properties of the cells are changed when the passage number exceeds a certain number, it is preferable to make the passage number as small as possible.

Thus, cryopreservation is usually performed if the properties are maintained consistently, i.e., cells are preserved, for a medium and long term. However, primate, especially human, ES cells and iPS cells are known to be sensitive to freezing and thawing and to have a low viability after cryopreservation. Therefore, frequent cryopreservation cannot be performed for primate pluripotent stem cells.

Meanwhile, for human ES cells and iPS cells, it is difficult to prepare cells of different origin to a desired cell concentration during the same period because the growth rate is different by established cell line. For human ES cells and iPS cells, it is recommended to change a medium every day due to their fast metabolism, and the risk of contamination is high, placing a burden on researchers.

Therefore, in culture of primate pluripotent stem cells such as human ES cells and iPS cells, methods for simply maintaining and preserving pluripotent stem cells without cell passage while maintaining the properties of pluripotent stem cells other than cryopreservation are required. In other words, methods for temporarily controlling the proliferation of pluripotent stem cells without changing the properties of the cells are required.

Xylose is one of the constituent sugars of sugar chains, and plays an important role in vivo, such as in intercellular communication. Xylose is also known to be abundantly contained in woody biomass, and the expansion of its use as unused resources in various fields has been required. However, in the field of culture cells, xylose has not been used as a saccharide in a medium because cells are considered not to be able to use xylose as energy.

The present inventors previously confirmed the effects of various saccharides (e.g., glucose, xylose, galactose, and the like) on mouse ES cells, and reported the possibility that xylose maintains the undifferentiation status and its cell proliferation effects in mouse ES cells (Tadayuki Yokoyama et al., Effects of various sugars on cell proliferation and EB formation of mouse ES cells, The 7th Congress of the Japanese Society for Regenerative Medicine, Program and Abstract, Vol. 7, pp. 239, 2008; Tadayuki Yokoyama et al., Xylose maintains the undifferentiation status of mouse ES cells, The 8th Congress of the Japanese Society for Regenerative Medicine, Program and Abstract, Vol. 8, pp. 221, 2009; Sakiko Takizawa-Shirasawa et. al., The 6th International Niigata Symposium on Diet and Health, pp. 152, 2012.)

However, these literatures have no description of primate pluripotent stem cells, which is remarkably sensitive to changes in culture environment compared with mouse ES cells. To the inventors' knowledge, there are no reports on the use of xylose for cells other than mouse ES cells.

The present inventors found this time that in human iPS cells, when a medium in which glucose contained in a commercially available common medium for human iPS cells is replaced by xylose is used, the viability can be maintained and cell proliferation can be inhibited while the undifferentiation status and the pluripotency are maintained. In other words, human iPS cells were successfully maintained and preserved without cryopreservation and passage while the properties of human iPS cells are maintained. Despite the fact that saccharides other than glucose had usually been considered not to be able to be used as energy in cells, it was surprising that the viability could be maintained and the cells could be maintained at normal culture temperature for a long time over 1 week while the undifferentiation status and the pluripotency, which tend to be lost by culture environment degradation, are maintained. The present invention is based on these findings.

SUMMARY OF THE INVENTION

Thus, it is an object of the present invention to provide a maintenance medium for primate pluripotent stem cells, a composition comprising primate pluripotent stem cells in contact with a maintenance medium, and a method for preserving and a method for controlling proliferation of primate pluripotent stem cells using the medium.

A maintenance medium for primate pluripotent stem cells according to the present invention includes xylose as a saccharide and is substantially free of glucose.

According to one aspect of the present invention, in the maintenance medium for primate pluripotent stem cells, primate pluripotent stem cells are human pluripotent stem cells.

According to one aspect of the present invention, in the maintenance medium for primate pluripotent stem cells, human pluripotent stem cells are human iPS cells.

According to one preferred aspect of the present invention, in the maintenance medium for primate pluripotent stem cells, a xylose concentration is 0.7 to 12.0 g/L at the final concentration.

According to one aspect of the present invention, in the maintenance medium for primate pluripotent stem cells, the medium is a culture medium for human iPS cells containing xylose in place of glucose.

According to one preferred aspect of the present invention, in the maintenance medium for primate pluripotent stem cells, the basal medium of a culture medium for human iPS cells is a DMEM/F12 medium.

According to one aspect of the present invention, a composition includes primate pluripotent stem cells in contact with a maintenance medium comprising xylose as a saccharide that is substantially free of glucose. The primate pluripotent stem cells in the composition can be human pluripotent stem cells. In one embodiment, the primate pluripotent stem cells are human iPS cells. The xylose concentration in the maintenance medium can be in a range of from 0.7 to 12.0 g/L at the final concentration. In one embodiment of the composition, the maintenance medium is a culture medium for human iPS cells containing xylose in place of glucose. A basal medium of the culture medium for human iPS cells can be a DMEM/F12 medium.

According to one aspect of the present invention, there is provided a method for preserving primate pluripotent stem cells, including the maintenance of primate pluripotent stem cells using a medium including xylose as a saccharide, which is substantially free of glucose.

According to one aspect of the present invention, a method for controlling proliferation of primate pluripotent stem cells which includes inhibiting the proliferation of primate pluripotent stem cells using a medium including xylose as a saccharide, which is substantially free of glucose, is provided.

According to one aspect of the present invention, the method for controlling proliferation further includes the promotion of the proliferation of primate pluripotent stem cells using a medium containing glucose.

According to the maintenance medium for pluripotent stem cells of the present invention, the undifferentiation status and the pluripotency of pluripotent stem cells can be maintained without the addition of undifferentiation-maintaining factors and cell proliferation can be inhibited under normal culture conditions. Therefore, a maintenance medium for pluripotent stem cells according to the present invention is extremely useful in the short-term preservation and the maintenance of pluripotent stem cells that are sensitive to freezing.

Xylose used in the present invention is abundantly contained in woody unused resources, and thus it is expected that the cost can be reduced.

Furthermore, a method for preserving and a method for controlling proliferation of pluripotent stem cells according to the present invention involve only the change of a normal medium with a maintenance medium for pluripotent stem cells of the present invention. Thus, the culture protocol for pluripotent stem cells need not be modified at all, and these methods do not require skill and are very simple.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRITION OF THE INVENTION

Maintenance Medium for Pluripotent Stem Cells

Figure 1A:
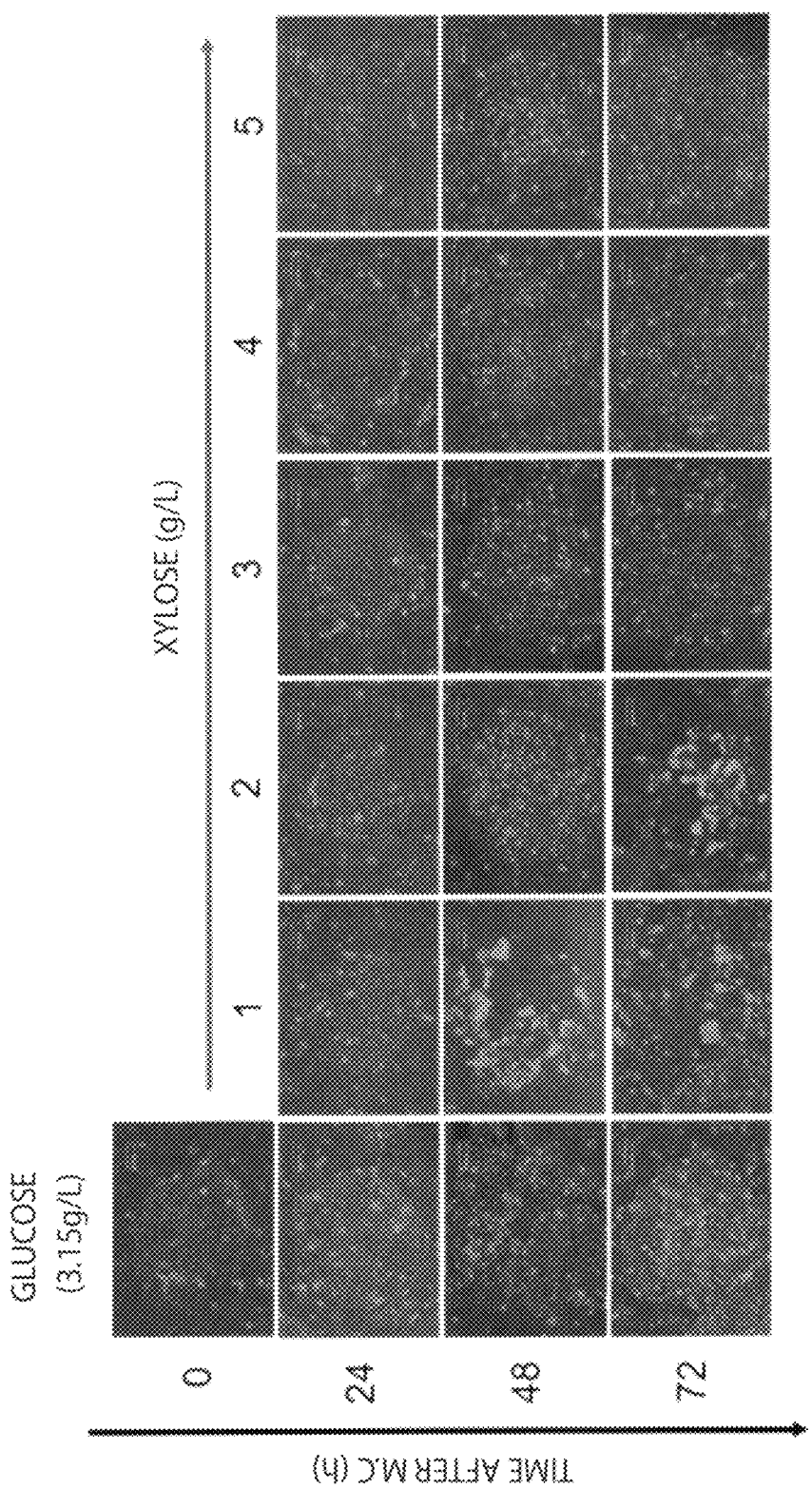
FIGS. 1A-1D show the results of microscopy when human iPS cell 253G1 lines of Example 1 were cultured in a glucose medium for iPS cells or xylose media for iPS cells at various concentrations (media of the present invention) (40 times magnification). The xylose media for iPS cells of (A) and (B) contain dialysed KSR, and the xylose media for iPS cells of (C) and (D) contain normal KSR that is not dialysed.
Figure 1B:
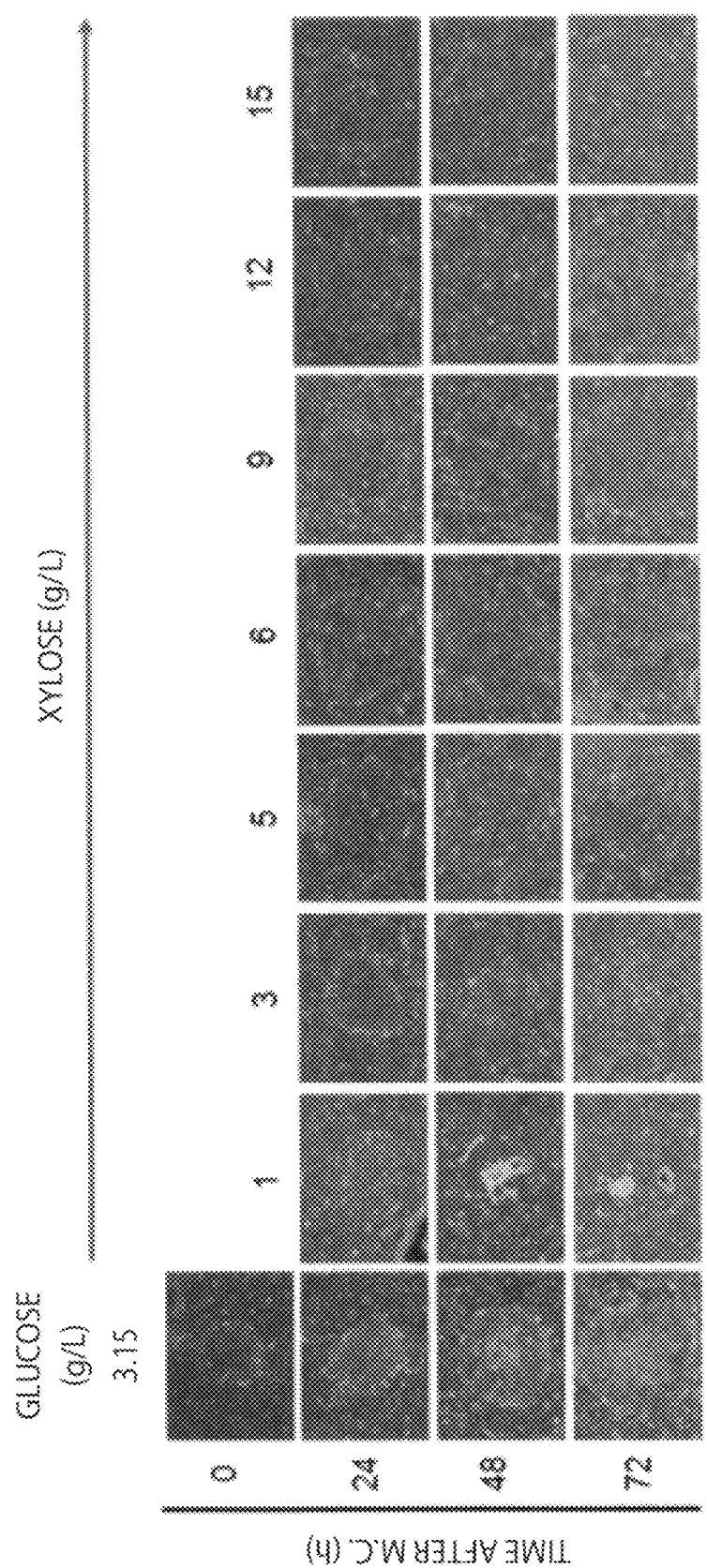
Figure 1C:
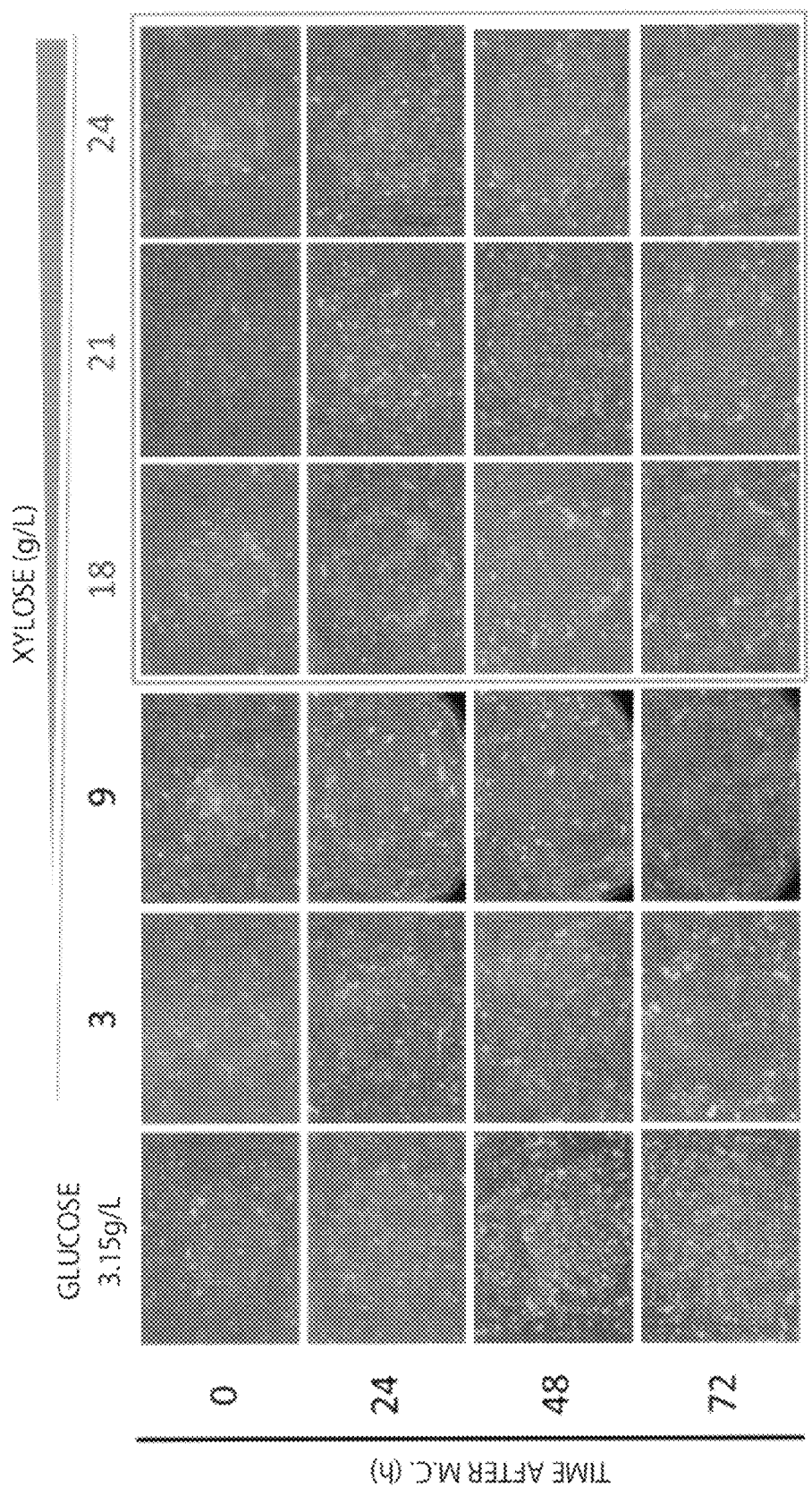
Figure 1D:
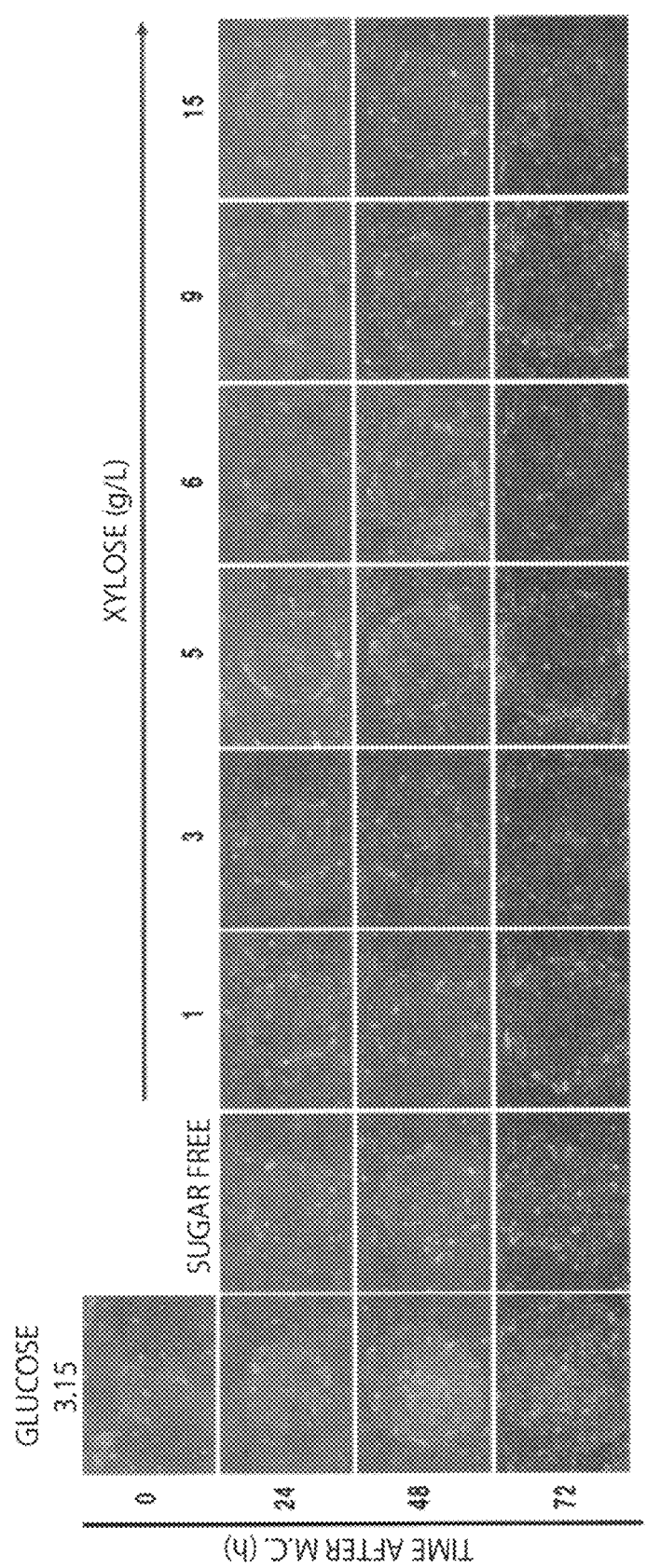

In the present specification, "primate pluripotent stem cells" mean pluripotent stem cells that can be artificially cultured ex vivo. Primates include humans, anthropoids such as orangutans, chimpanzees, and gorillas, prosimians, and monkeys. In the present specification, "pluripotent stem cells" mean cells having self-renewal capacity that produce a cell the same as their own, and having pluripotency, which means differentiation into other types of cells constituting tissues and organs. Pluripotent stem cells include, for example, embryonic stem cells (ES cells), induced pluripotent stem cells (iPS cells), embryonic germ cells (EG cells), embryonal carcinoma cells (EC cells), and adult pluripotent stem cells (APS cells). Primate pluripotent stem cells used in the present invention are preferably human pluripotent stem cells, more preferably human ES cells or iPS cells, and still more preferably human iPS cells. These pluripotent stem cells can be obtained by methods well known to a person skilled in the art, or commercially available pluripotent stem cells can be used.

"Pluripotency" means the ability to differentiate into all differentiated cells belonging to ectoderm, mesoderm, or endoderm, and the property of being able to differentiate into at least one type of differentiated cells each belonging to ectoderm, mesoderm, or endoderm, and can include the differentiation potency into germ cells. Differentiated cells can differentiate into many types of cells constituting body tissues and organs in the future. Whether cells have pluripotency or not can be determined by, for example, transplantation of pluripotent stem cells into SCID mice to form teratoma and subsequent evaluation of whether triploblastic (ectodermal, mesodermal, and endodermal) cells are differentiated and formed from the morphology, or by in situ expression of various differentiation markers.

"Undifferentiation status" means that cells are not differentiated into a certain cell lineage yet, and stem cells located relatively higher in the hierarchy have this property. Whether cells have undifferentiation status or not can be determined by measurement of undifferentiated cell markers and differentiation markers. Specifically, if undifferentiated cell markers are expressed and the expression of differentiation markers is low, it can be considered that undifferentiation status is maintained. In the case of human pluripotent stem cells, undifferentiation markers used in the present invention include, for example, Oct-4, Nanog, NodaI, Sox2, TDGF, DNMT3B, ZFP42, SSEA3, SSEA4, and TRA1-60, and differentiation markers include, for example, BCL6B, FOXN4, GATA6, Brachyury, and EOMES.

Xylose used as a saccharide in a maintenance medium for pluripotent stem cells of the present invention abounds in woody biomass, and a monosaccharide of pentose also called wood sugar. Xylose used in the present invention may be D-xylose, which abounds in nature, or may be L-xylose or DL-xylose prepared by synthesis. Xylose used in the present invention is preferably D-xylose in terms of low-cost preparation.

In the present specification, "maintenance medium for pluripotent stem cells" means a medium suitable for maintenance of pluripotent stem cells or its composition, and a medium that enables the survival of a certain number of the cells for a certain period without significant damage affecting the viability of the cells while maintaining the undifferentiation status and the pluripotency of pluripotent stem cells. Specifically, use of maintenance medium for pluripotent stem cells of the present invention can inhibit the proliferation of pluripotent stem cells while maintaining the properties, i.e., undifferentiation status and pluripotency, of pluripotent stem cells.

A maintenance medium for pluripotent stem cells of the present invention can maintain the undifferentiation status and the pluripotency of pluripotent stem cells if the maintenance medium for pluripotent stem cells contains xylose as a saccharide even when the medium does not substantially contain undifferentiation-maintaining factors. In other words, xylose contained in the maintenance medium for pluripotent stem cells of the present invention has undifferentiation-maintaining effects on pluripotent stem cells.

"Saccharide" means an energy source to be metabolized by cells immersed in a medium for their survival. A saccharide contained in a medium of the present invention is xylose, and glucose is not substantially included. A saccharide contained in a medium of the present invention includes xylose, and may further include saccharides other than glucose, and preferably includes only xylose.

The term "not substantially contain glucose" or "substantially free of glucose" means that glucose is not contained in a medium, or even if glucose is contained, the amount of glucose contained is such that cells cannot use it as a saccharide, i.e., an energy source. Specifically, the amount of glucose for the total amount of saccharides (100% by weight) contained in a medium is desirably less than 20% by weight, preferably less than 15% by weight, more preferably less than 10% by weight, still more preferably less than 7% by weight, yet more preferably less than 5% by weight, further preferably less than 4% by weight, further preferably less than 3% by weight, further preferably less than 2% by weight, further preferably less than 1% by weight, further preferably less than 0.5% by weight, and particularly preferably less than 0.1% by weight.

Metabolism of xylose by cells enables the cell proliferation inhibitory effects, which are objects of the present invention. "Cell proliferation inhibitory effects" mean maintenance of the viability of cells and inhibition of cell proliferation. Inhibition of cell proliferation enables the maintenance and preservation of cells at a constant condition.

When converted into the amount of saccharides, the metabolism of xylose by cells is less than the metabolism of glucose (refer to Example 3(1) mentioned below). Therefore, use of a maintenance medium for pluripotent stem cells of the present invention can inhibit cell proliferation, and due to a low metabolism of saccharides by cells, does not require daily medium change, which is needed in normal culture, and can reduce the burden on researchers.

Whether xylose is metabolized as a saccharide or not can be determined by measurement of phosphoribosyl pyrophosphate (PRPP). The present inventors found that PRPP is a metabolite specific to xylose metabolism, and a substance that is not produced by glucose metabolism or shows an extremely high value (refer to Example 3(2) mentioned below). Therefore, the measurement of PRPP as a xylose metabolism marker can confirm the metabolism of xylose. Specifically, PRPP in cells or culture supernatants can be measured with CE-TOFMS, HPLC, or LC-MSMS. Other than PRPP, NADP$^+$, NAD$^+$, IMP, nicotinamide, or xanthine, which shows a higher value than glucose metabolism, can be used as a xylose metabolism marker. These substances can be measured with the same methods as for PRPP.

Whether glucose is metabolized as a saccharide or not can be determined by measurement of glucose 6-phosphate, fructose 1,6-diphosphate, glyceraldehyde 3-phosphate, pyruvic acid, or kynurenine. These substances can be measured with the same methods as for PRPP.

The content of xylose in a maintenance medium for pluripotent stem cells of the present invention is 0.7 g/L or more, preferably 0.7 to 12.0 g/L, more preferably 2.3 to 12.0 g/L, still more preferably 2.3 to 9.0 g/L, and yet more preferably 2.3 to 4.7 g/L at the final concentration for human pluripotent stem cells. The content of xylose for the basal medium before preparation of a maintenance medium for pluripotent stem cells of the present invention is 1.0 g/L or more, preferably 1.0 to 15.0 g/L, more preferably 3.0 to 15.0 g/L, still more preferably 3.0 to 9.0 g/L, and yet more preferably 3.0 to 6.0 g/L. Since xylose has no toxicity and is well water soluble, addition of a large amount of xylose usually causes no substantial problems, but the amount is desirably up to 24 g/L for a basal medium in terms of osmotic pressure and cost.

A maintenance medium for pluripotent stem cells of the present invention can be obtained by containing xylose in place of glucose in a conventional medium used for pluripotent stem cell culture, i.e., a normal culture medium for pluripotent stem cells for proliferation. Specifically, a maintenance medium for pluripotent stem cells of the present invention can be obtained by, as needed, adding serum or serum substitutes or other components to a basal medium in which glucose is replacement with xylose in the medium. The proportion of replacement of glucose by xylose is desirably more than 80%, preferably more than 90%, more preferably more than 93%, still more preferably more than 95%, yet more preferably more than 96%, further preferably more than 97%, further e preferably more than 98%, further preferably more than 99%, further preferably more than 99.5%, further preferably more than 99.9%, and particularly preferably 100%.

A basal medium include, for example, Dulbecco's modified Eagle's medium (DMEM), Eagle's minimal essential medium (MEM), Ham's F12 medium, DMEM/F12 medium, MCDB medium, Fisher's medium, RPMI-1640 medium, and feeder-free medium (Essential 8™ medium (Life Technologies Corporation)).

All serum or serum substitutes can be used if publicly known. For example, serum includes FBS and FCS, and serum substitutes include KSR, and the like.

Other components include non-essential amino acids, pH adjustment agents, and the like.

If glucose in contained in serum or serum substitutes or other components added to a basal medium, it is preferable to remove glucose by membrane treatment. Membrane treatment can be performed by, for example, using a dialysis membrane 36/32 (manufactured by EIDIA Co., Ltd.). Since KSR does not substantially contain glucose, dialysis may not be performed.

According to one aspect of the present invention, there is provided a method for preserving primate pluripotent stem cells, which includes maintening primate pluripotent stem cells using a medium including xylose as a saccharide, which does not substantially contain glucose.

The term "maintaining primate pluripotent stem cells" means a procedure in which primate pluripotent stem cells are immersed in a maintenance medium for pluripotent stem cells of the present invention and placed under normal culture conditions. The maintenance can inhibit cell proliferation and preserve cells for a short period while the undifferentiation status and the pluripotency of pluripotent stem cells are maintained. In a method for preserving of the present invention, during preservation, an only certain number of pluripotent stem cells need to survive and pluripotent stem cells may proliferate. The proportion of proliferation only needs to be lower than that when a normal culture medium containing glucose is used.

According to the method for preserving of the present invention, daily medium change need not be performed. Thus, risk of contamination due to daily medium change can be avoided, and the burden on researchers can be reduced.

As long as the undifferentiation status and the pluripotency are maintained, the preservation period can be changed as appropriate depending on the type of cells cultured, culture objective, the type of a basal medium, or culture temperature. If daily medium change is not performed, the period is preferably 4 days, and more preferably 2 days. If daily medium change is performed, the period is preferably 6 days, and more preferably 3 days.

According to one aspect of the present invention, there is provided a method for controlling proliferation of primate pluripotent stem cells, which includes inhibiting the proliferation of primate pluripotent stem cells using a medium including xylose as a saccharide, which does not substantially contain glucose.

The term "cell proliferation control" means a procedure in which cell proliferative capacity is stopped at a desired time, the cell concentration is maintained without significant damage affecting the viability of cells to the cells, and subsequently cell proliferation is restarted at a desired time. In other words, in a method for controlling cell proliferation of the present invention, the proliferation of primate pluripotent stem cells can be inhibited with a maintenance medium for pluripotent stem cells of the present invention, and after a desired period elapsed, the proliferation of primate pluripotent stem cells can be promoted with a culture medium containing glucose. In a method for controlling cell proliferation of the present invention, the growth rate and the morphology of pluripotent stem cells following the procedure in which the proliferation is inhibited with a maintenance medium for pluripotent stem cells of the present invention, and after an inhibition period passed, the proliferation is restarted by change the medium with a normal culture medium for pluripotent stem cells containing glucose are almost same as those when pluripotent stem cells are cultured only in a normal culture medium for pluripotent stem cells. Thus, in a method for controlling cell proliferation of the present invention, cell proliferation control can be performed without affecting the proliferative capacity of pluripotent stem cells. Furthermore, the method for controlling cell of the present invention can only be performed by replacement a maintenance medium for pluripotent stem cells of the present invention by a normal culture medium for pluripotent stem cells containing glucose.

When plural types of primate pluripotent stem cells are prepared and subjected to an experiment, since the growth rate differs by type of pluripotent stem cells, even if a desired cell concentration is obtained and the experiment is prepared for certain pluripotent stem cells, the experiment for other pluripotent stem cells with a slow growth rate may not be prepared. In such cases, when a method for controlling proliferation of primate pluripotent stem cells of the present invention is used, the conditions for all cells subjected to an experiment can easily be arranged by replacing the medium for prepared primate pluripotent stem cells by a maintenance medium for pluripotent stem cells of the present invention and by preserving the cells until other pluripotent stem cells are prepared.

Cell proliferation control may be performed at normal cell culture temperature and under normal cell culture environment conditions.

As long as the undifferentiation status and the pluripotency are maintained, the cell proliferation inhibition period can be changed as appropriate depending on the type of cells cultured, culture objective, the type of a basal medium, or culture temperature. If daily medium change is not performed, cell proliferation can be inhibited for at least 5 days, and more preferably at least 2 days. If daily medium change is performed, the period is preferably 10 days, and more preferably 5 days.

EXAMPLES

Examples of the present invention will be described in detail below. However, the present invention is not limited by these Examples.

Example 1

Culture of Human iPS Cells (253G1 Lines and 201B7 Lines) in a Xylose Medium (1) Preparation of Medium A medium for human iPS cells (induced pluripotent stem cells) was prepared each so that the composition was as follows.

Control Medium (Glucose Medium for iPS Cells):

DMEM/F12 (Gibco BRL, Rockville, Md.), 20 volume % KSR (Invitrogen), 2 mM L-glutamine (Gibco), 1×MEM non-essential amino acid solution (Wako), 100 µM β-mercaptoethanol (Sigma, St. Louis, Mo.), 50 U/mL penicillin and 50 µg/mL streptomycin (Gibco BRL), and 4 ng/mL basic FGF (Invitrogen).

Medium According to Present Invention (Xylose Medium for iPS Cells):

Modified DMEM/F12 containing D-xylose at various concentrations in place of glucose contained in a normal DMEM/F12 (M-DMEM, available from Nissui Pharmaceutical Co., Ltd.), 20 volume % KSR (Invitrogen) or 20 volume % dialysed KSR (available from Nissui Pharmaceutical Co., Ltd.) in which sugars (saccharides) are removed by a dialysis membrane (dialysis membrane 36/32, manufactured by EIDIA Co., Ltd.), 2 mM L-glutamine (Gibco), 1×MEM non-essential amino acid solution (Wako), 100 µM β-mercaptoethanol (Sigma, St. Louis, Mo.), 50 U/mL penicillin and 50 µg/mL streptomycin (Gibco BRL), and 4 ng/mL basic FGF (Invitrogen).

Xylose concentrations in a modified DMEM/F12 were prepared so that the xylose concentrations contained in a basal medium before medium preparation, a DMEM/F12, were 0, 1, 2, 3, 4, 5, 6, 9, 12, 15, 18, 21, and 24 g/L. In this example, unless mentioned as a final concentration, the concentration of xylose or glucose represents a concentration for a basal medium before medium preparation. The final concentration of xylose in a medium after preparation can be calculated from the xylose concentration in a basal medium before medium preparation × 77.5%. Since addition of xylose is associated with variation of osmotic pressure, adjustment was performed by adding sodium chloride in order to the osmotic pressure was same as that in a normal DMEM/F12, i.e., a glucose medium for iPS cells (glucose concentration: 3.15 g/L) (specifically, value: 290 to 350 mOsm). In terms of osmotic pressure, the critical concentration of xylose concentration was 24 g/L.

(2) Preparation of Human iPS Cells

As human iPS cells, 253G1 lines and 201B7 lines (both were available from iPS Academia Japan, Inc.) were used. The 253G1 lines were human iPS (induced pluripotent stem) cell lines established by introducing 3 factors (Oct3/4, Sox2, and Klf4) with retroviral vectors, and the 201B7 lines were human iPS cell lines established by introducing 4 factors (Oct3/4, Sox2, Klf4, and c-Myc) were introduced into retroviral vectors.

Each of the human iPS cells (253G1 lines and 201B7 lines) was cultured on a layer of MEF feeder cells (available from Oriental Yeast Co., Ltd.) inactivated with mitomycin C (Sigma) in a cell culture dish (6-well plate, available from Sanplatec Corporation) coated with 0.1% by weight gelatin (Sigma) at 37° C. in the presence of 5% $CO_2$. The above mentioned glucose medium for iPS cells was used, and medium change was performed daily.

(3) Property Study of Human iPS Cells

After iPS cells were cultured on MEF feeder cells, only a colony of the iPS cells was recovered using a dissociation solution (1× trypsin (Gibco), 1 mg/mL collagenase type IV (Gibco), 20% KSR (Gibco), 10 mM $CaCl_2$ (Wako), and 1×PBS (Wako)), and then the iPS cells were seeded on a 60 mm dish (available from AGC Techno Glass Co., Ltd.) on which inactivated MEF feeder cells were seeded with the number of cells of 0.6 to $1.8×10^5$, and were cultured with the above mentioned glucose medium for iPS cells at 37° C. in the presence of 5% $CO_2$ for 24 hours to form a colony again.

After colony formation, the colony was cultured by changing the glucose medium for iPS cells with xylose media for iPS cells containing xylose at various concentrations (defined as "0 hour after medium change (M.C.)"). The colony was cultured also in a control medium (glucose medium for iPS cells). During culture period, medium change was performed daily.

For each iPS cell colony, observation of the morphology, confirmation of differentiation tendency by gene expression analysis (RT-qPCR), and pluripotency study were performed.

Observation of Colony Morphology

Figure 2A:
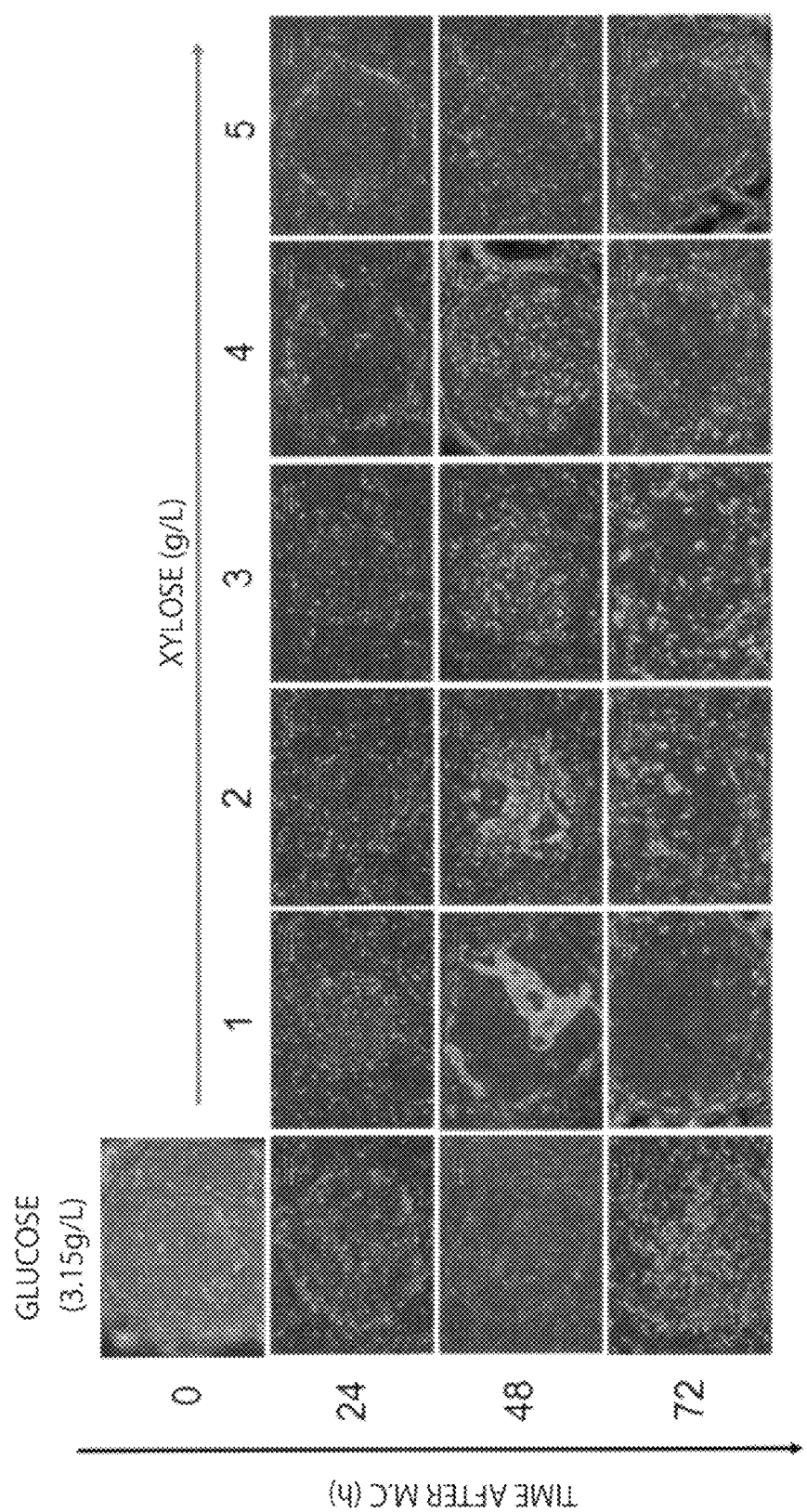
FIGS. 2A-2B show the results of microscopy when human iPS cell 201B7 lines of Example 1 were cultured in a glucose medium for iPS cells or xylose media for iPS cells at various concentrations (media of the present invention) (40 times magnification). The xylose media for iPS cells of (A) and (B) contain dialysed KSR.
Figure 2B:
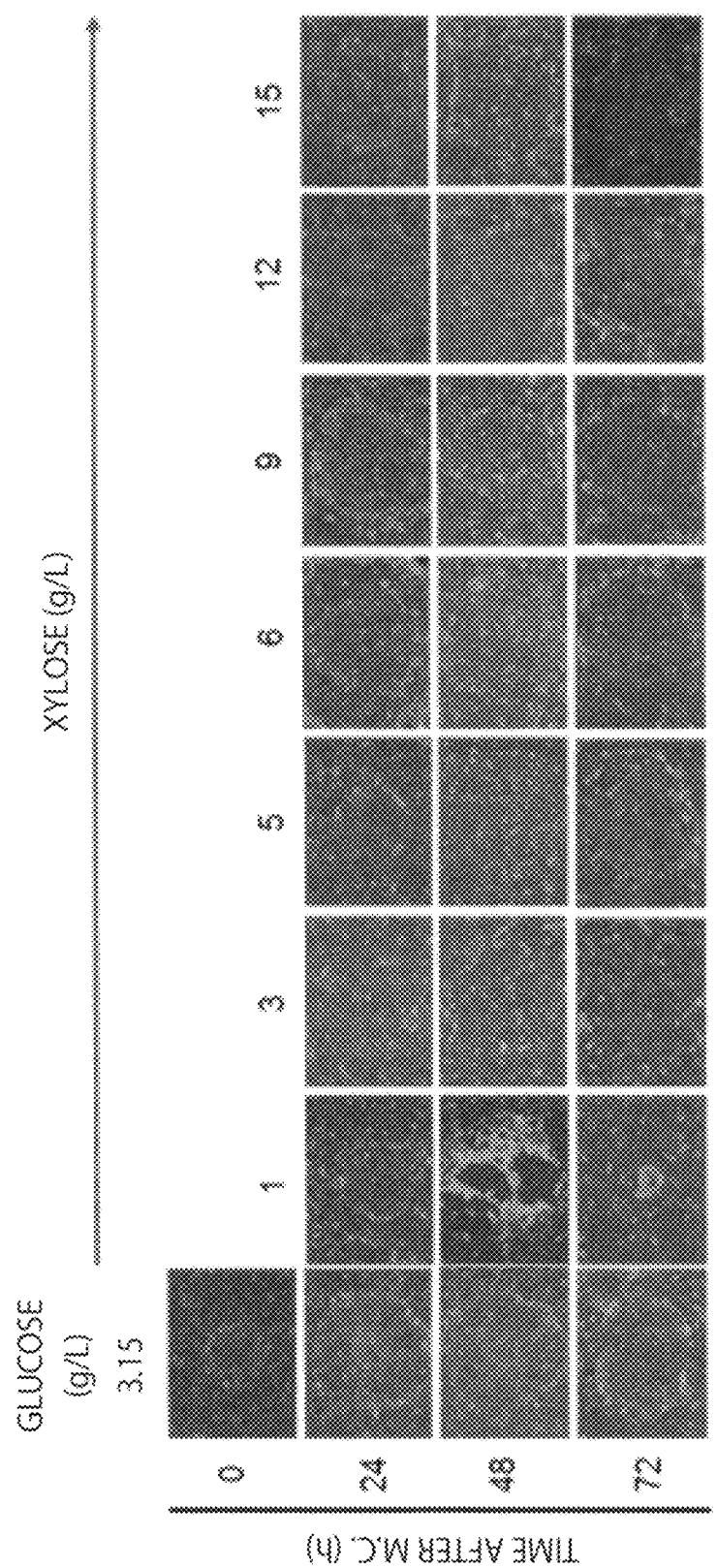

The morphology of iPS cell colonies at 0, 24, 48, and 72 hours after medium change was observed with a light microscope (IX70, manufactured by Olympus Corporation). The results of 253G1 lines are shown in FIGS. 1A and B (dialysed KSR) and FIGS. C and D (KSR), and the results of 201B7 lines are shown in FIGS. 2A and B (dialysed KSR).

As shown in the results, in a xylose medium for iPS cells containing xylose, no changes in colony morphology were observed compared with a control medium, and the size of a colony was small. In other words, the inhibition of cell proliferation can be confirmed. In a control medium, many floating dead cells were also observed, and it is considered that after 72 hours of medium change, a xylose medium for iPS cells is more suitable as a culture condition. Furthermore, when the xylose concentration was 5 g/L or more, there were no differences in effects of concentration on the morphology, i.e., the inhibition of proliferation and the maintenance of undifferentiation status were observed. When the concentration was 2 g/L or less, the collapse of a colony was observed. At about 24 g/L, which is the critical concentration, the compactness of a colony was slightly decreased and a colony showing a differentiation tendency was observed. In 253G1 lines and 201B7 lines, there were no differences between iPS cell lines. There were also no differences between KSR and dialysed KSR. Both KSR and dialysed KSR did not contain glucose (analysis by HPLC-RI).

Figure 3:
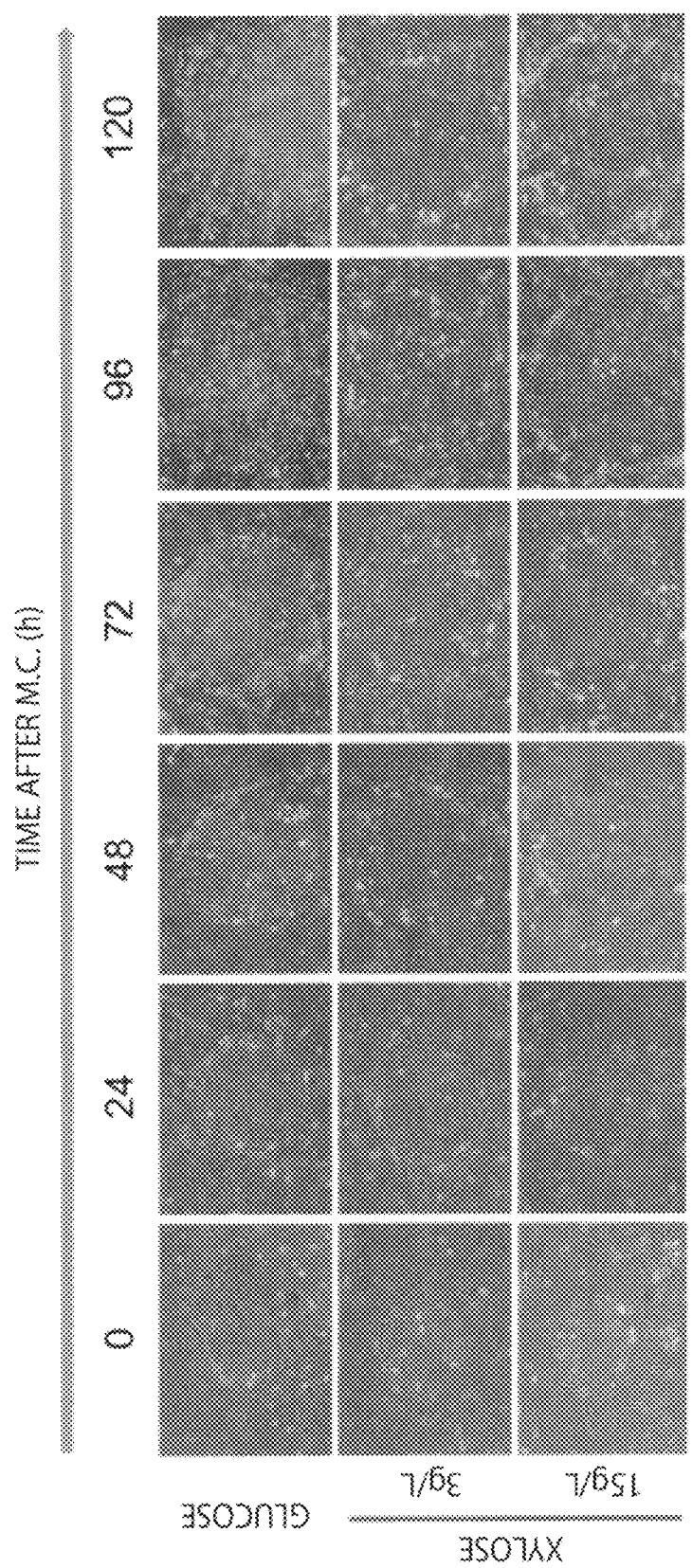
FIG. 3 shows the results of microscopy when human iPS cell 253G1 lines of Example 1 were cultured for 120 hours in a glucose medium for iPS cells or xylose media for iPS cells at concentrations of 3 g/L or 15 g/L (media of the present invention) (40 times magnification). The xylose media for iPS cells contain normal KSR that is not dialysed.

For a xylose medium for iPS cells in which xylose concentrations were 3 g/L and 15 g/L, the morphology of iPS cell colonies at 96 and 120 hours after culture was also observed with a light microscope (IX70, manufactured by Olympus Corporation). The results are shown in FIG. 3 (253G1 lines, KSR).

As shown in the results, in a control medium, when a long-term culture was performed, a colony became excessively larger, the colony morphology became difficult to be maintained, and many floating dead cells were observed. On the other hand, in a xylose medium for iPS cells, cell proliferation was inhibited, the colony morphology was good while performing a long-term culture, and the number of floating dead cells was small.

Figure 4:
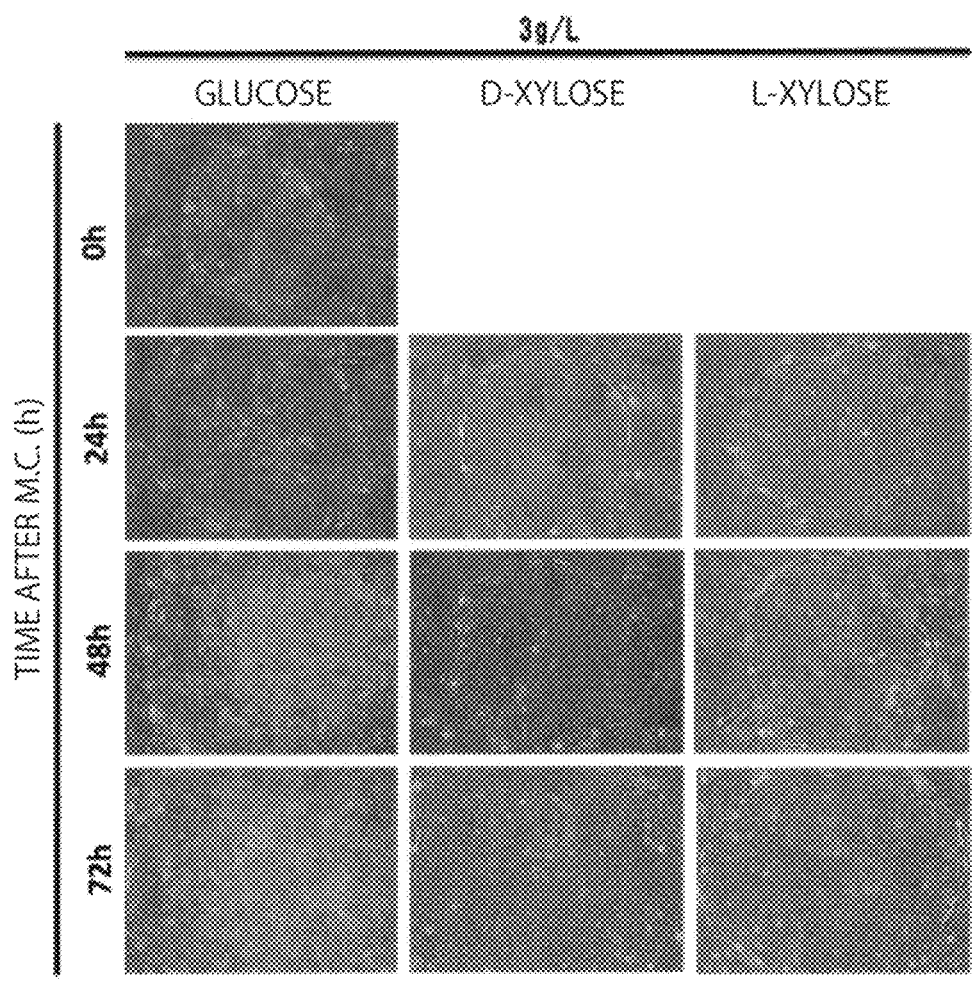
FIG. 4 shows the results of microscopy when human iPS cell 253G1 lines of Example 1 were cultured in a glucose medium for iPS cells or a D- or L-xylose medium for iPS cells (a medium of the present invention) (40 times magnification). The D- or L-xylose medium for iPS cells contains normal KSR that is not dialysed.
Figure 5A:
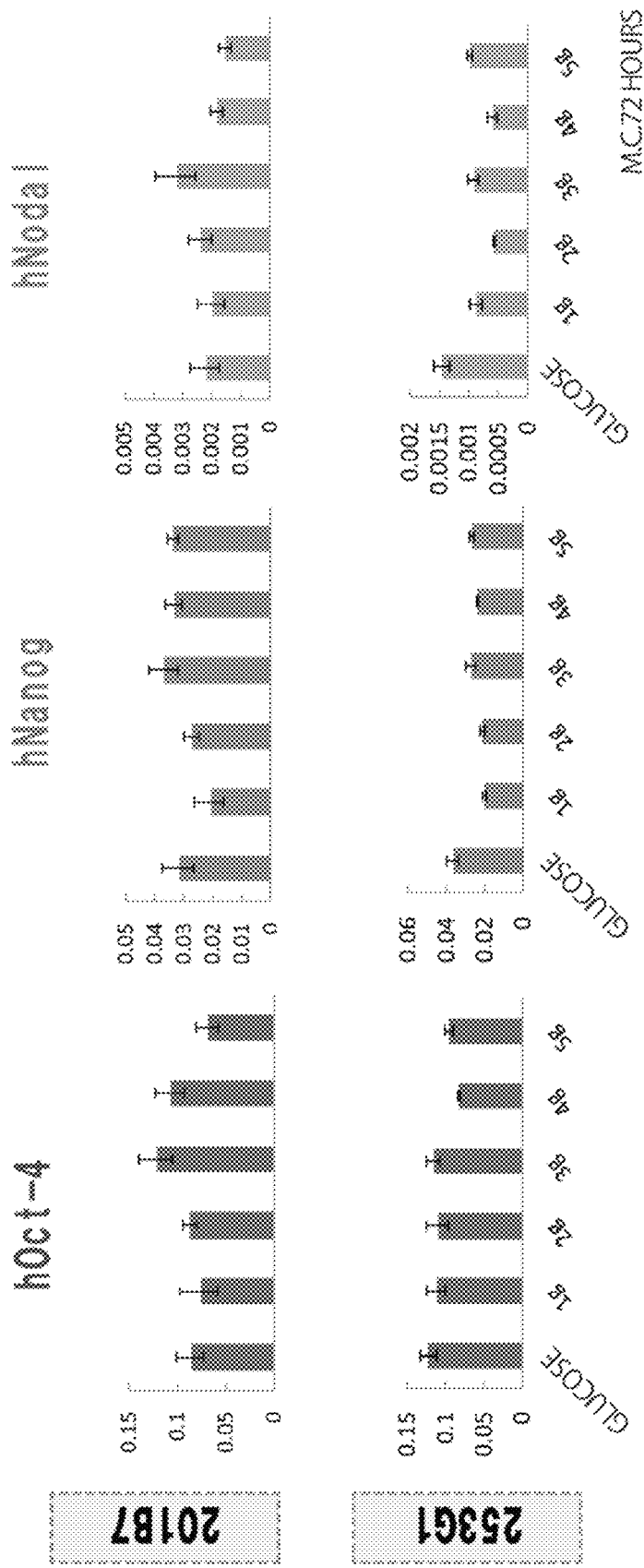
FIG. 5A-5D show the results of RT-qPCR when human iPS cell 253G1 lines and 201B7 lines of Example 1 were cultured in a glucose medium for iPS cells or xylose media for iPS cells at various concentrations (media of the present invention). The xylose media for iPS cells contain normal KSR that is not dialysed.
Figure 5B:
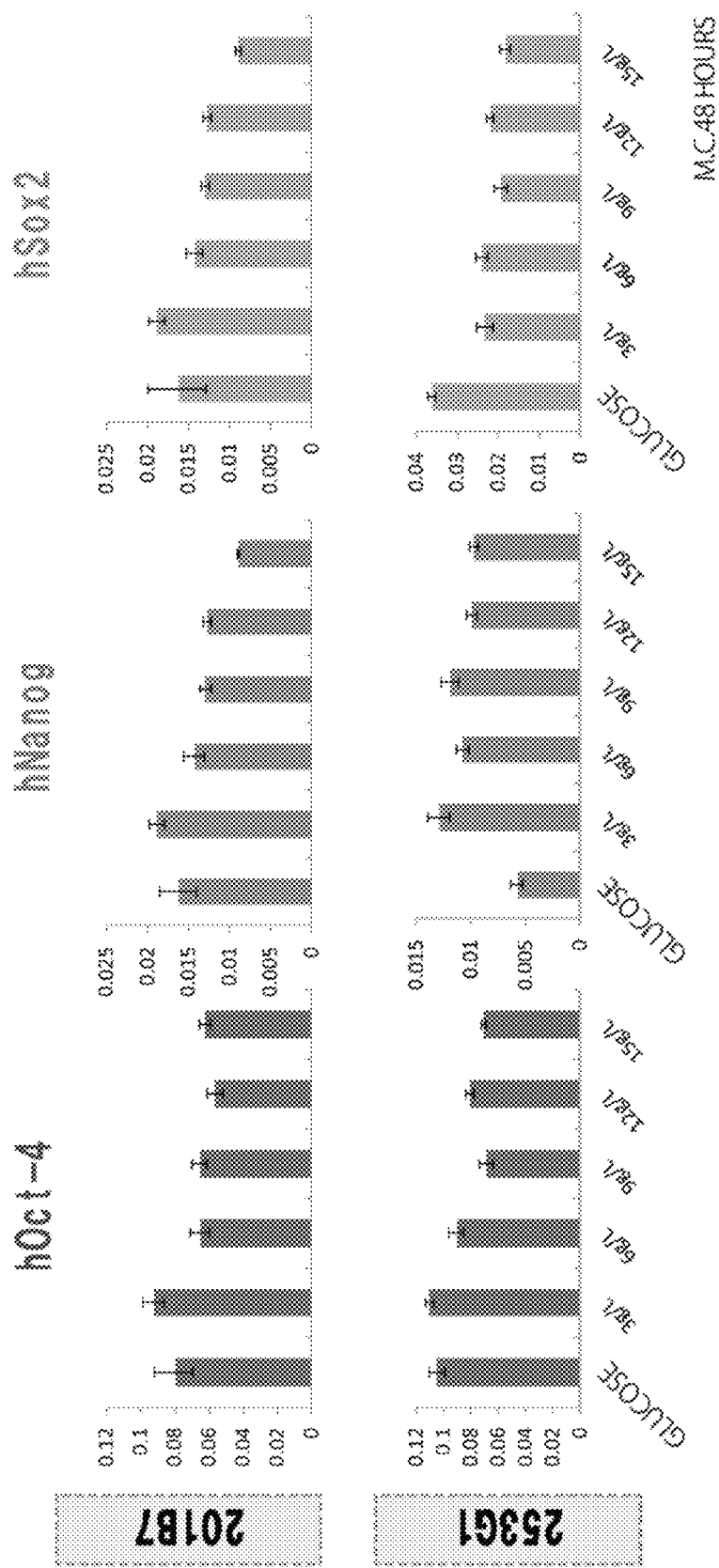
Figure 5C:
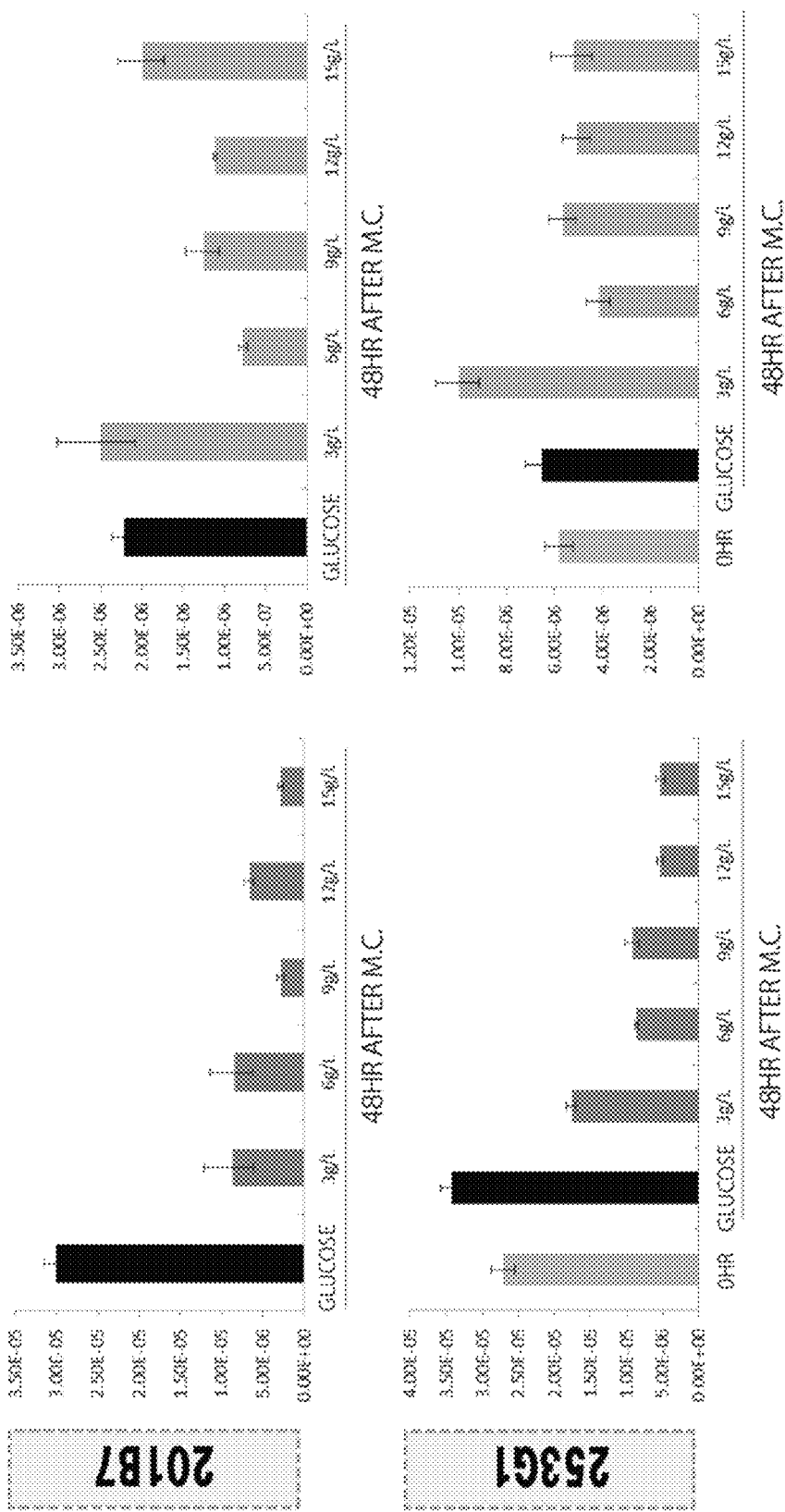
Figure 5D:
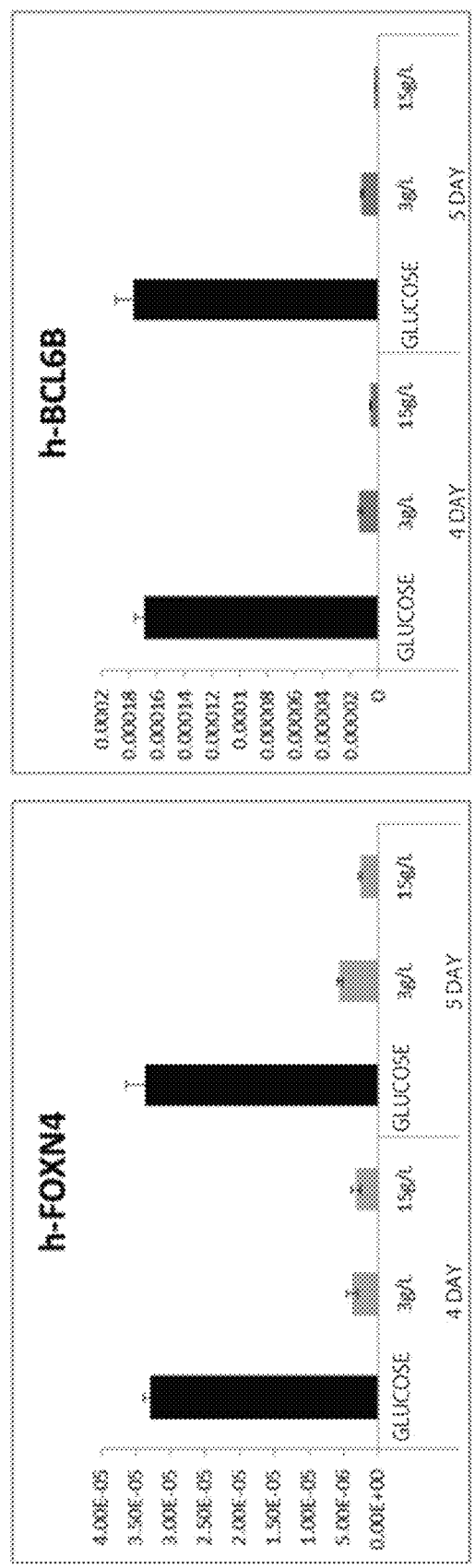

In addition, for a xylose medium for iPS cells in which xylose concentration was 3 g/L, a medium containing L-xylose (L-substance) in place of D-xylose (D-substance) was prepared, and the morphology of iPS cell colonies at 0, 24, 48, and 72 hours after culture was observed with a light microscope (IX70, manufactured by Olympus Corporation). The results are shown in FIG. 4 (253G1 lines, KSR).

As shown in the results, there were no differences in colony morphology and proliferation inhibitory effects between D-xylose and L-xylose.

Gene Expression Analysis (RT-qPCR)

All RNAs of a colony of iPS cells (253G1 lines and 201B7 lines) at 48 or 72 hours after they were cultured in xylose media for iPS cells at various concentrations were extracted with a TRIzol reagent (Invitrogen, Carlsbad, Calif.). From the extracted RNAs, cDNAs were prepared with Super Script II (Invitrogen). cDNA samples were amplified with hOct-4, hNanog, hNodal, and hSox2 as an undifferentiation marker and h-BCL6B and h-FOXN4 as a differentiation marker of the primers in the following Table 1 (Thermal Cycler Dice, manufactured by Takara Bio Inc.).

Pluripotency Test

Figure 6:
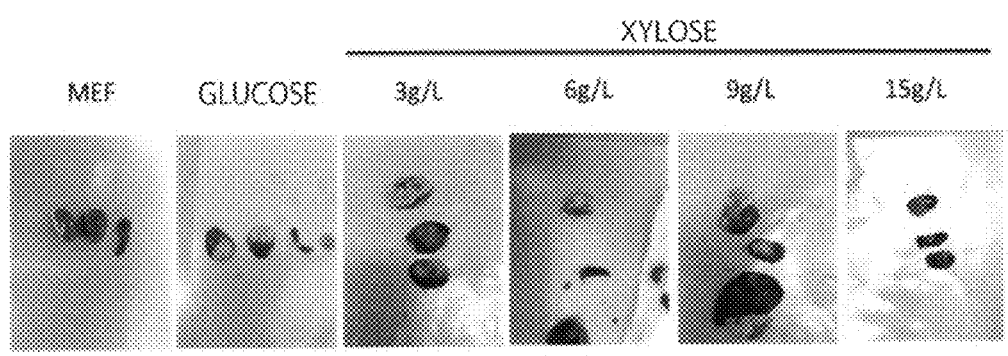
FIG. 6 is a photograph showing each organ recovered at 4 weeks after transplantation of human iPS cell 253G1 lines that were cultured for 24 hours in a glucose medium for iPS cells or a xylose medium for iPS cells of Example 1 or feeder cells into the kidney and the spleen of SCID mice. The xylose medium for iPS cells contains normal KSR that is not dialysed.

Human iPS cells (253G1 lines) cultured in xylose media for iPS cells at concentrations of 3, 6, 9, and 15 g/L and in a glucose medium for iPS cells and MEF feeder cells were recovered at 24 hours after culture, and 1 to $4 \times 10^6$ cells were transplanted into the kidney and the spleen of SCID mice (available from CLEA Japan, Inc.). At 4 weeks after transplantation, the kidney and the spleen were recovered from each mouse. The presence or absence of tumor (teratoma) formation in the organs was evaluated. The results are shown in FIG. 6.

Figure 7:
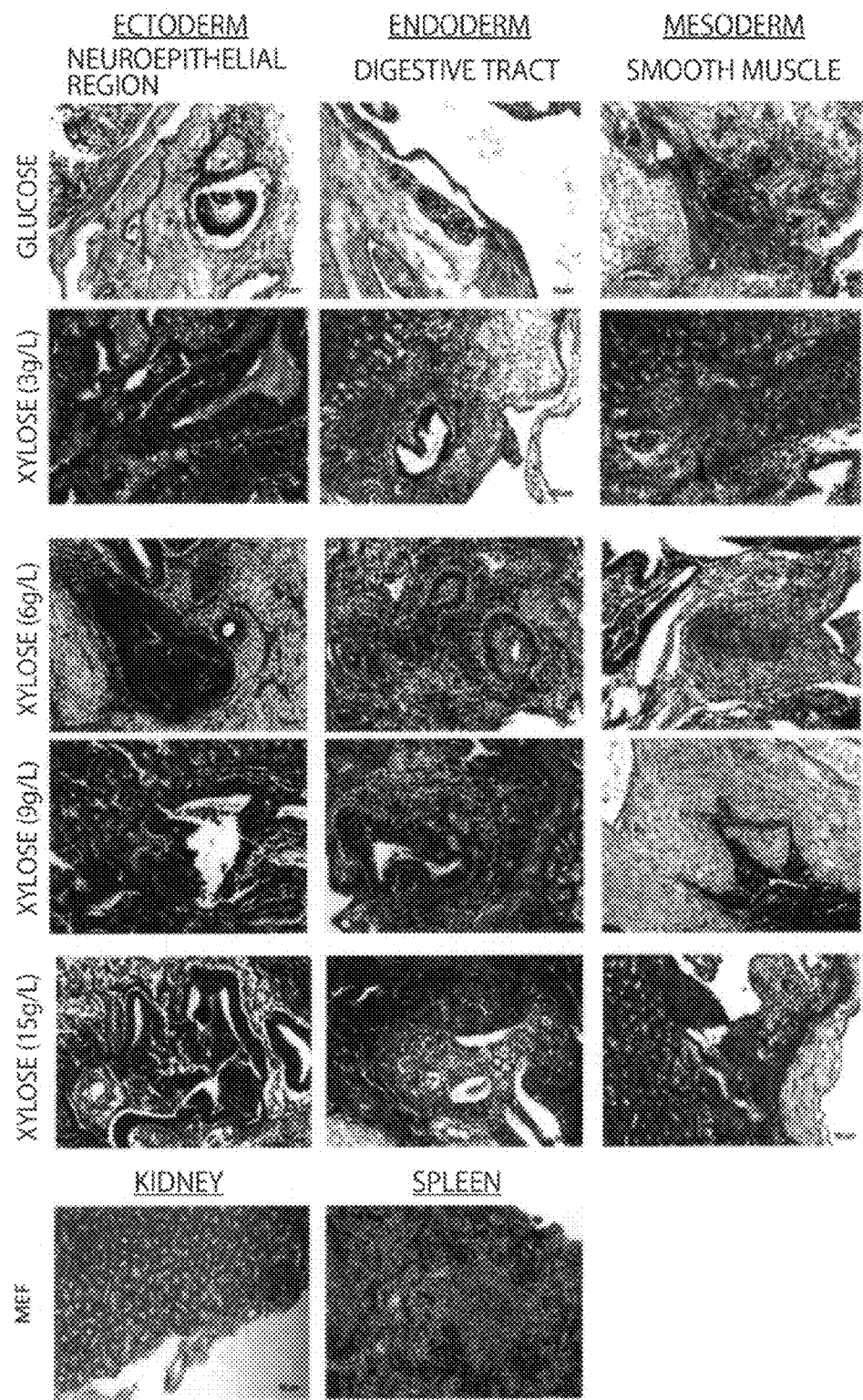
FIG. 7 shows the results of microscopy of HE staining of a paraffin section of each organ recovered at 4 weeks after transplantation of human iPS cell 253G1 lines that were cultured for 24 hours in a glucose medium for iPS cells or a xylose medium for iPS cells of Example 1 or feeder cells into the kidney and the spleen of SCID mice (200 times magnification). The xylose medium for iPS cells contains normal KSR that is not dialysed.

Paraffin blocks were prepared from each organ obtained in accordance with conventional methods, and HE staining was performed to evaluate differentiation into triploblastic cells. The results are shown in FIG. 7.

As shown in the results, although no tumors were observed in the organs into which MEF feeder cells were transplanted, tumor formation was observed in the organs into which iPS cells were transplanted. In other words, since tumors could be formed by transplanting iPS cells cultured in a xylose medium for iPS cells, it could be confirmed that infinite proliferation, an important function of iPS cells, was maintained regardless of xylose concentration. Triploblastic

TABLE 1

| Primer Name | Type | Sequence |
|---|---|---|
| hOct-4 | Undifferentiation marker | Forward: TCTATTTGGGAAGGTATTCAGC SEQ ID NO: 1 |
|  |  | Reverse: ATTGTTGTCAGCTTCCTCCA SEQ ID NO: 2 |
| hNanog | Undifferentiation marker | Forward: AGCTACAAACAGGTGAAGAC SEQ ID NO: 3 |
|  |  | Reverse: GGTGGTAGGAAGAGTAAAGG SEQ ID NO: 4 |
| hNodal | Undifferentiation marker | Forward: AGACATCATCCGCGACCTA SEQ ID NO: 5 |
|  |  | Reverse: CAAAAGCAAACGTCCAGTTCT SEQ ID NO: 6 |
| hSox2 | Undifferentiation marker | Forward: GGGGGAATGGACCTTGTATAG SEQ ID NO: 7 |
|  |  | Reverse: GCAAAGCTCCTACCGTACCA SEQ ID NO: 8 |
| h-BCL6B | Differentiation marker | Forward: GAACGGGCTCGTCCACTAC SEQ ID NO: 9 |
|  |  | Reverse: CCCCAGGAACCAAGGAGT SEQ ID NO: 10 |
| h-FOXN4 | Differentiation marker | Forward: CCCAAGCCCATCTACTCGT SEQ ID NO: 11 |
|  |  | Reverse: GTAGGGGAAGTGCTCCTTCAT SEQ ID NO: 12 |
| β-actin | Control marker | Forward: CATCCGTAAAGACCTCTATGC-CAAC SEQ ID NO: 13 |
|  |  | Reverse: ATGGAGCCACCGATCCACA SEQ ID NO: 14 |
| Amplification condition |  | 95° C., 3 min. → (95° C., 3 min. → annealing temperature of each primer, 30 sec., 72° C., 30 sec.) × 35 cycles |

The results are shown in FIGS. 5A to D. As is clear from the results, in the iPS cells cultured in a xylose medium for iPS cells, the expression of an undifferentiation marker equivalent to that in a glucose medium for iPS cells was observed at 48 and 72 hours after medium change. In the iPS cells cultured in a xylose medium for iPS cells, almost no expression of a differentiation marker was observed compared with that in a glucose medium for iPS cells, and almost no expression of a differentiation marker was observed even at 96 and 120 hours after medium change (refer to FIG. 5D). In other words, it was revealed that in iPS cells cultured in a xylose medium for iPS cells, the undifferentiation function was maintained and the differentiation was inhibited. In 253G1 lines and 201B7 lines, there were no differences between iPS cell lines.

cell-forming ability was confirmed in all iPS cells; in other words, it could be confirmed that pluripotency is maintained even when cells are cultured in a xylose medium for iPS cells.

(4) Cell Proliferation Control

Figure 8:
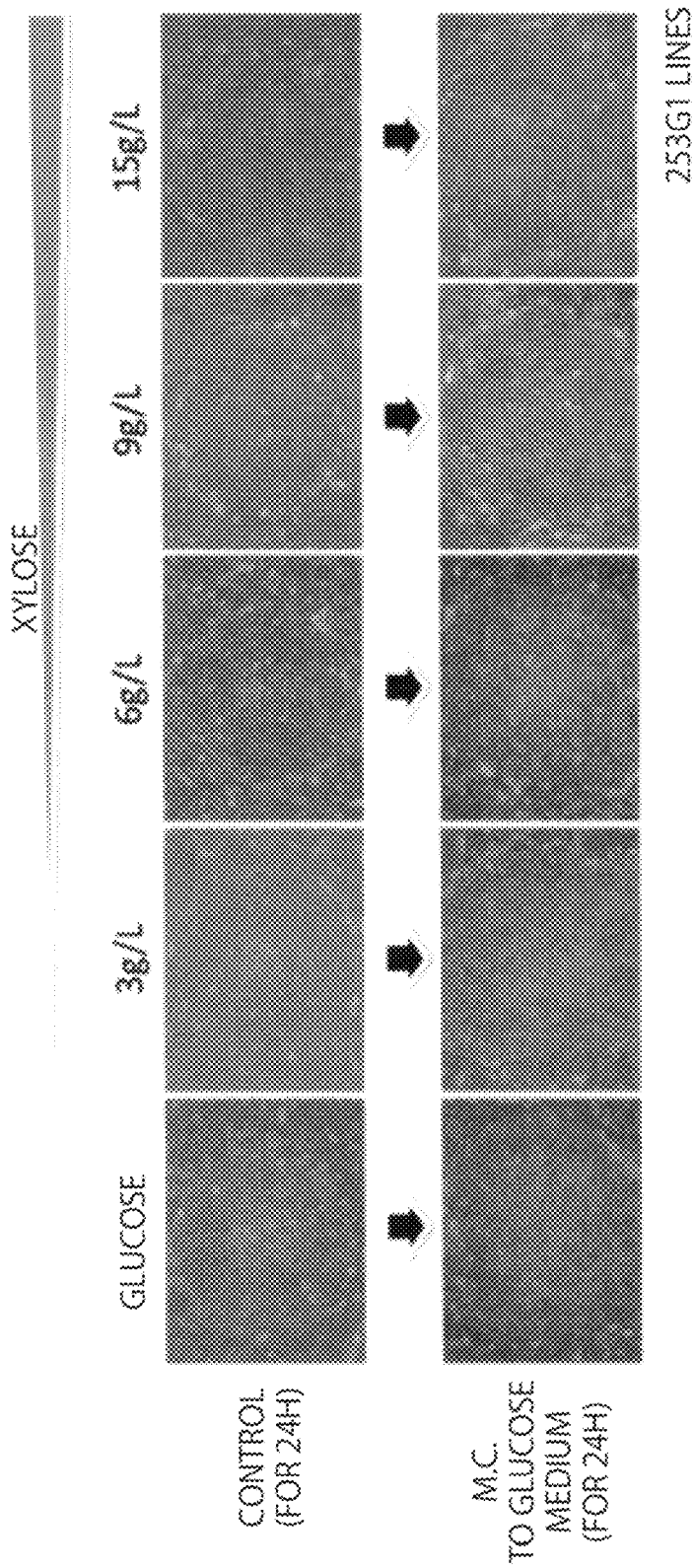
FIG. 8 shows the results of microscopy when a colony of the human iPS cell 253G1 lines of Example 1 was cultured by changing a glucose medium for iPS cells with xylose media for iPS cells at various concentrations, the media were changed with a glucose medium for iPS cells again at 24 hours after culture, and the cells were cultured in the glucose medium for iPS cells for 24 hours (40 times magnification). The xylose media for iPS cells contain normal KSR that is not dialysed.

A colony was formed in accordance with the methods mentioned in the above (3), and the glucose medium for iPS cells was replaced by xylose media for iPS cells at concentrations of 3, 6, 9, and 15 g/L, and a colony of iPS cells (253G1 lines) were cultured in the xylose media. At 24 hours after culture, the media were changed again with a glucose medium for iPS cells. At 24 hours after change, the morphology of iPS cells was observed. The results are shown in FIG. 8.

As shown in the results, when a xylose medium for iPS cells was changed with a glucose medium for iPS cells, any effects on the morphology were not observed, and proliferation was restarted. In other words, it was revealed that only by changing a xylose medium for iPS cells of the present invention with a glucose medium for iPS cells, proliferation of human iPS cells can be simply controlled.

Example 2

Cell Proliferation Control of Human iPS Cells (Disease iPS Cells Derived from Ehlers-Danlos Syndrome Patients (P-iPS Cells))

(1) Preparation of Medium

A medium for human iPS cells (induced pluripotent stem cells) was prepared each so that the composition was as follows.

Control Medium (Glucose Medium for iPS Cells):
DMEM/F12 (Gibco BRL, Rockville, Md.), 20 volume % KSR (Invitrogen), 2 mM L-glutamine (Gibco), 1×MEM non-essential amino acid solution (Wako), 100 µM β-mercaptoethanol (Sigma, St. Louis, Mo.), 50 U/mL penicillin and 50 µg/mL streptomycin (Gibco BRL), and 4 ng/mL basic FGF (Invitrogen).

Medium According to Present Invention (Xylose Medium for iPS Cells):
Modified DMEM/F12 in which glucose contained in a normal DMEM/F12 is changed with D-xylose (M-DMEM, available from Nissui Pharmaceutical Co., Ltd.) (D-xylose concentration: 3.15 g/L), 20 volume % dialysed KSR (available from Nissui Pharmaceutical Co., Ltd.) in which sugars are removed by a dialysis membrane (dialysis membrane 36/32, manufactured by EIDIA Co., Ltd.), 2 mM L-glutamine (Gibco), 1×MEM non-essential amino acid solution (Wako), 100 µM β-mercaptoethanol (Sigma, St. Louis, Mo.), 50 U/mL penicillin and 50 µg/mL streptomycin (Gibco BRL), and 4 ng/mL basic FGF (Invitrogen).

(2) Preparation of Human iPS Cells

As human iPS cells, disease iPS cells derived from the nerve cells of Ehlers-Danlos syndrome patients (available from Shinshu University) (hereinafter referred to as "P-iPS") were used. The P-iPS cells were cultured on a layer of MEF feeder cells (available from Oriental Yeast Co., Ltd.) inactivated with mitomycin C (Sigma) in a cell culture dish (6-well plate, available from Sanplatec Corporation) coated with 0.1% by weight gelatin (Sigma) at 37° C. in the presence of 5% $CO_2$. The above mentioned glucose medium for iPS cells was used, and medium change was performed daily.

(3) Proliferation Inhibitory Effects of Human iPS Cells

After P-iPS cells were cultured on MEF feeder cells, only a colony of the P-iPS cells was recovered using 0.25% by weight trypsin and 0.1 mg/mL collagenase IV (Invitrogen); then, the P-iPS cells were seeded on a 96-well plate (available from AGC Techno Glass Co., Ltd.) on which inactivated MEF feeder cells were seeded, and were cultured with the above mentioned glucose medium for iPS cells at 37° C. in the presence of 5% $CO_2$ for 4 days to form a colony again.

After colony formation, the colony was cultured by changing one medium with a xylose medium for iPS cells (defined as "0 days after culture").

At 8 days after culture, P-iPS cells cultured in a xylose medium for iPS cells were further cultured for 8 days by changing the medium with a glucose medium for iPS cells again. During culture period, medium change was performed daily.

At 0, 1, 4, and 8 days after culture and at 1, 4, and 8 days after the medium was changed with a glucose medium again (9, 12, and 16 days after culture), cell viability was measured by MTT assay. MTT assay was performed for 6 wells each time.

MTT Assay

Measurement was performed in accordance with the product manual with MTT Cell Growth Assay Kit (Chemicon). Specifically, 100 µL of the medium of cells cultured in a 96-well plate was replaced by a fresh medium, 10 µL of a MTT reagent was added to this medium, and the cells were incubated for 4 hours. Then, the formazan dye (blue) produced by living cells was dissolved by adding a lysate (0.04N HCl/isopropanol) and pipetting several times, and measurement was performed with absorption wavelength of 570 nm and reference wavelength of 630 nm using a plate reader. For the viability, mean±SD of each was calculated by defining the value on 0 days after culture as 100%.

Figure 9A:
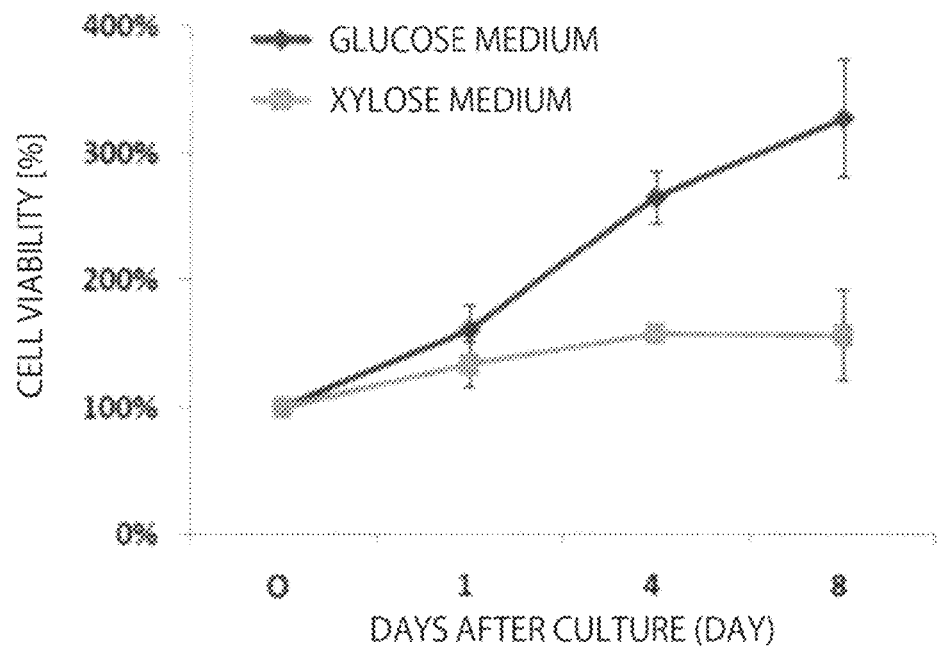
FIG. 9A-9B are graphs showing the cell viability evaluated by a MU assay when human iPS cells (disease iPS cells derived from Ehlers-Danlos syndrome patients (P-iPS cells)) of Example 2 were cultured in a glucose medium for iPS cells or a xylose medium for iPS cells. The graph (A) shows the cell viability when the cells were cultured in each medium for 8 days, and the graph (B) shows the cell viability when the cells were cultured in each medium for 8 days, the medium was changed with a normal glucose medium, and the cells were further cultured for 8 days.
Figure 9B:
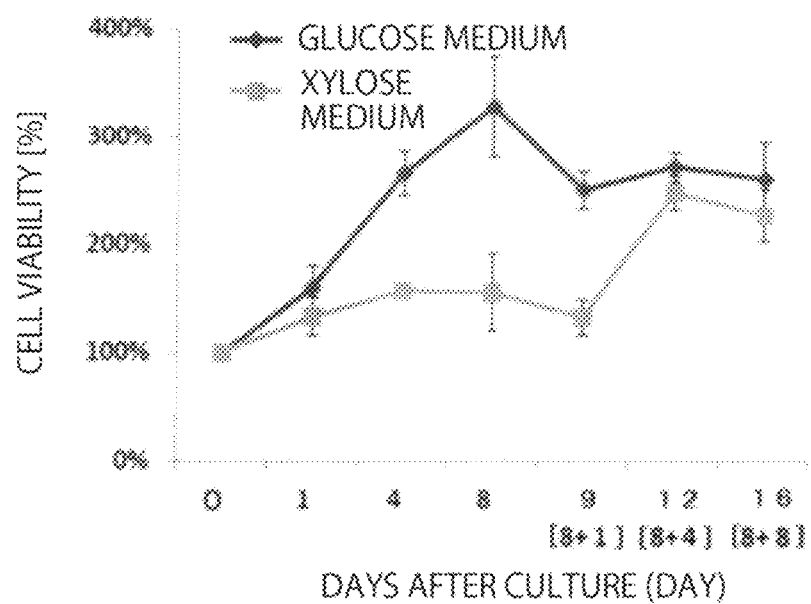

The results are shown in FIGS. 9A and B.

Example 3

Metabolites of Human iPS Cells in Xylose Medium (1) Saccharide Consumption in Each Medium iPS cells (253G1 lines) were cultured for 24 hours with a xylose medium for iPS cells or a glucose medium for iPS cells, the consumption of each saccharide(sugar) contained in the supernatant after culture was calculated. Measurement of each saccharide was performed with HPLC (manufactured by Shimadzu Corporation). When the amount at 0 hours after culture was defined as 100.0, the sugar amount was 79.0 for a glucose medium for iPS cells and 88.2 for a xylose medium for iPS cells, and when converted into sugar consumption (%), it was 21.1% and 11.8%, respectively.

(2) Confirmation of Metabolites

For metabolites in cell samples when iPS cells (253G1 lines) were cultured in a xylose medium for iPS cells, metabolome analysis were performed. Specifically, cell samples and culture supernatants were deproteinized by ultrafiltration, and the relative area of detected substances among metabolites registered in the HTM metabolite library was calculated with CE-TOFMS (manufactured by Agilent Technologies, Inc.). As a control, those in a glucose medium for iPS cells or a xylose stable isotope medium containing the stable isotope ($^{13}C$) of xylose (available from Omicron Biochemicals, Inc.) were also analyzed. From the analysis results, metabolites specific to each medium were identified as a metabolism marker of each medium. The results are shown in Tables 2 and 3.

TABLE 2

Metabolism Markers of Xylose

| Metabolite Name | Glucose Medium for iPS Cells | Xylose Medium for iPS Cells ($^{12}C$) | Xylose Stable Isotope Medium ($^{13}C$) |
|---|---|---|---|
| PRPP | N.D. | 3.5E−03 | N.D. |
| NADP⁺ | 3.4E−03 | 4.7E−03 | 1.7E−03 |
| NAD⁺ | 1.2E−01 | 1.6E−01 | 3.2E−02 |
| IMP | 1.1E−03 | 1.6E−03 | N.D. |
| Nicotinamide | 7.8E−05 | 1.0E−04 | N.D. |
| Xanthine | N.D. | 1.6E−05 | 3.1E−05 |

N.D.: Not Detected

TABLE 3

| | Metabolism Markers of Glucose | | |
|---|---|---|---|
| Metabolite Name | Glucose Medium for iPS Cells | Xylose Medium for iPS Cells ($^{12}C$) | Xylose Stable Isotope Medium ($^{13}C$) |
| Glucose 6-phosphate | 4.8E−02 | 3.0E−03 | N.D. |
| Fructose 1,6-diphosphate | 2.7E−01 | N.D. | N.D. |
| Glyceraldehyde 3-phosphate | 9.5E−03 | N.D. | N.D. |
| Pyruvic acid | 1.0E−03 | N.D. | N.D. |
| Kynurenine | 7.7E−05 | N.D. | N.D. |

N.D.: Not Detected

As shown in the results, it was revealed that PRPP was specifically contained as a metabolite in iPS cells cultured in a xylose medium for iPS cells or their culture supernatants. This PRPP was not contained when cells were cultured in a glucose medium for iPS cells, i.e., was found to be a specific metabolite in a xylose medium.

What is claimed is:

1. A method for controlling proliferation of primate pluripotent stem cells, which comprises inhibiting the proliferation of primate pluripotent stem cells using a medium comprising xylose as a saccharide, which is substantially free of glucose.

2. The method according to claim 1, which further comprises promoting the proliferation of primate pluripotent stem cells using a medium comprising glucose.

3. The method according to claim 1, wherein the primate pluripotent stem cells are human pluripotent stem cells.

4. The method according to claim 1, wherein the primate pluripotent stem cells are human iPS cells.

5. The method according to claim 1, wherein the xylose concentration is 0.7 to 12.0 g/L at the final concentration.

6. The method according to claim 1, wherein the medium is a culture medium for human iPS cells containing xylose in place of glucose.

7. The method according to claim 6, wherein a basal medium of the culture medium for human iPS cells is a DMEM/F12 medium.

8. A method for maintaining primate pluripotent stem cells, which comprises maintaining the undifferentiation status and the pluripotency of the primate pluripotent stem cells using a medium, comprising xylose as a saccharide, which is substantially free of glucose.

9. The method according to claim 8, wherein the primate pluripotent stem cells are human pluripotent stem cells.

10. The method according to claim 8, wherein the primate pluripotent stem cells are human iPS cells.

11. The method according to claim 8, wherein the xylose concentration is 0.7 to 12.0 g/L at the final concentration.

12. The method according to claim 8, wherein the medium is a culture medium for human iPS cells containing xylose in place of glucose.

13. The method according to claim 12, wherein a basal medium of the culture medium for human iPS cells is a DMEM/F12 medium.

* * * * *